US006661868B2

(12) United States Patent
Sawada

(10) Patent No.: US 6,661,868 B2
(45) Date of Patent: Dec. 9, 2003

(54) RADIATION INSPECTION APPARATUS AND RADIATION INSPECTION METHOD

(75) Inventor: Ryoichi Sawada, Joyo (JP)

(73) Assignee: Shimadzu Corporation, Kyoto (JP)

(*) Notice: Subject to any disclaimer, the term of this patent is extended or adjusted under 35 U.S.C. 154(b) by 0 days.

(21) Appl. No.: 10/123,756

(22) Filed: Apr. 16, 2002

(65) Prior Publication Data
US 2002/0150206 A1 Oct. 17, 2002

(30) Foreign Application Priority Data
Apr. 17, 2001 (JP) .......................... 2001-118629

(51) Int. Cl.⁷ .......................... G01N 23/04; G06K 9/03
(52) U.S. Cl. .......................... 378/57; 378/58; 382/143
(58) Field of Search .......................... 378/51, 53, 54, 378/56, 57, 58, 98.2, 98.8; 250/308, 358; 382/143; 348/254, 255, 256

(56) References Cited

U.S. PATENT DOCUMENTS 3,828,193 A * 8/1974 Nelson .......................... 378/86
5,585,603 A * 12/1996 Vogeley, Jr. .......................... 177/25.13
6,215,845 B1 * 4/2001 Knigge .......................... 378/57
6,335,960 B2 * 1/2002 Knigge et al. .......................... 378/57
6,347,131 B1 * 2/2002 Gusterson .......................... 378/54

* cited by examiner

Primary Examiner—Edward J. Glick
Assistant Examiner—Allen C. Ho
(74) Attorney, Agent, or Firm—Rankin, Hill, Porter & Clark LLP

(57) ABSTRACT

A radiation inspection apparatus is configured in such a way as to totalize pixels, whose gray levels represented by pixel gray level information, which is outputted from radiation detector, are within a preset gray level range of gray level profile from XL to XH, and to inspect from a result of the totalization whether or not a stockout of object occurs. Thus, the apparatus is enabled to correctly determine an occurrence of a stockout of the object by simple data processing without performing pattern recognition on a radiation perspective image.

5 Claims, 5 Drawing Sheets

RADIATION INSPECTION APPARATUS AND RADIATION INSPECTION METHOD

BACKGROUND OF THE INVENTION

1. Field of the Invention

The present invention relates to a non-destructive inspection apparatus or method for inspecting drugs and food-products. More particularly, the present invention relates to a radiation inspection apparatus and a radiation inspection method suitable for inspecting occurrences of a stockout of a packaged object, whose inside cannot be observed with visual light owing to packaging materials.

2. Description of the Related Art

Hitherto, an inspection apparatus using visual or infrared light has been known as an apparatus for inspecting occurrences of a stockout of a packaged food-product. This inspection apparatus using visual light or infrared light usually irradiates an object to be inspected with visual or infrared light and then receives light reflected or transmitted by the object by using a CCD camera. Thus, the inspection apparatus obtains image information concerning the inside of a package and determines the number of objects included in the package according to the shape thereof.

Meanwhile, in recent years, many kinds of aluminum foil and boxes, which are disabled to transmit light, have been employed as the manners of packaging food-products and drugs. Such inspection apparatuses using light are no use to inspect an occurrence of a stockout of the object packaged in such a manner.

Moreover, the inspection apparatus using light has a problem that, even if a packaging material constituted by a light-transmissive material is used, a result of inspection is significantly affected by the coloring of the surface of the packaging material.

It is sufficient for seeing the inner situation of the package wrapped by the packaging material made of a non-transmissive material therethrough to use an inspection apparatus using radiation, such as X-rays. In a conventional radiation inspection apparatus, radiation transmitted through the object to be inspected is detected by a one-dimensional or two-dimensional radiation detector. Then, a pattern of a perspective two-dimensional image of the object contained in the package is recognized by performing image processing using pixel information. Thus, the conventional apparatus determines whether or not a stockout of the object included in the package occurs according to the pattern thereof. Therefore, the conventional apparatus has problems that large-scale image processing should be performed so as to realize a high-speed inline system, and that both the hardware and software of the apparatus are too costly.

SUMMARY OF THE INVENTION

The invention is accomplished in view of such circumstances. Accordingly, an object of the invention is to provide a radiation inspection apparatus and a radiation inspection method that does not need large-scale image processing, which is needed by the conventional apparatus, and that is enabled to use the hardware and software for image processing, which are relatively simple, and to determine with a low-cost configuration whether or not a stockout of an object packaged by a non-transmissive material occurs. As used herein, the term "stockout" is meant to indicate either the condition wherein one or more objects are missing from the package or wherein one or more inferior or defective objects are included in the package.

To achieve the foregoing object, according to the invention, there is provided a radiation inspection apparatus, which comprises a radiation generator for generating radiation toward an object to be inspected; a radiation detector, disposed in such a way to face the radiation generator, for detecting the radiation transmitted through the object to be inspected and outputting a pixel gray level information for each pixel consisting an image of the object to be inspected; and a data processor unit for performing data processing by using the pixel gray level information outputted from the radiation detector. In this apparatus, the data processor unit totalizes the number of pixels, whose gray levels represented by the pixel gray level information, which is outputted from the radiation detector, are within a predetermined gray level range, and determines from a totalization of the number of pixels whether or not a stockout of the object to be inspected occurs.

The invention achieves the desired purpose by employing simple data processing, that is, totalizing the number of pixels, whose pixel gray levels are within the predetermined gray level range, and determining from a result of the totalization of the number of pixels whether or not a stockout of the object occurs, instead of performing pattern recognition of a perspective image by image processing using pixel information outputted from the radiation detector.

That is, pixels of a radiation perspective image of the object contained in the package have gray levels, which differ from those of pixels of other parts thereof. Thus, such a perspective image can be visually checked. Therefore, the gray levels of pixels of the object of a perspective image are included in a gray level range differing from a gray level range that includes the gray levels of pixels of other parts of the image. Such a gray level range can preliminarily be known. Thus, the gray level range is preliminarily set. Further, the number of pixels having gray levels included in the set gray level range is totalized. Thus, there is a correlation between a result of the totalization of the number of such pixels and the projected area of the object contained in the package. For example, in the case that the objects to be inspected are commodities, which are objects arranged in a certain direction and accommodated in a packaging container, the result of the totalization of the number of pixels is proportional to the number of the objects obtained in the packaging container. Therefore, it can correctly be determined by totalization of the number of pixels, whose gray levels are within the predetermined gray level range, of the radiation perspective image whether or not a stockout of the objects contained in the package occurs.

DETAILED DESCRIPTION OF THE INVENTION

Hereinafter, an embodiment of the invention is described with reference to the accompanying drawings.

Figure 1:
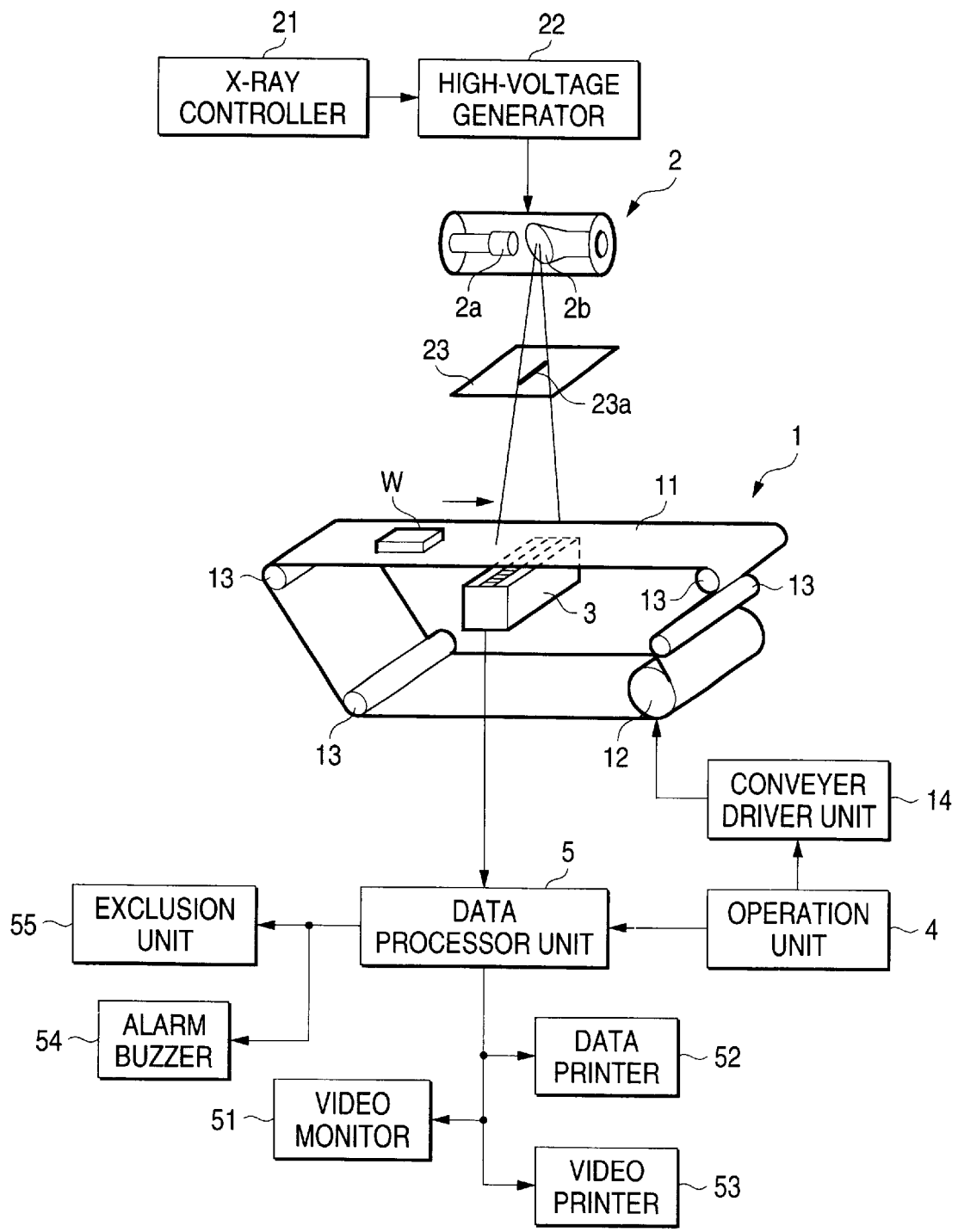
FIG. 1 is a view illustrating the configuration of a radiation inspection apparatus according to an embodiment of the invention.

FIG. 1 is a view illustrating the configuration of a radiation inspection apparatus according to an embodiment of the invention and describing both of a schematic diagram, which shows a mechanical configuration of a primary part of the embodiment, and a block diagram that shows a system control line of the primary part of the embodiment.

An object to be inspected W is put on a loop belt 11 of a conveyer system 1 and conveyed at a constant speed. Above the conveyer system 1, an X-ray tube 2 is disposed in a position in which an X-ray optical axis thereof is directed perpendicularly and downwardly. Moreover, a one-dimensional X-ray detector 3 is disposed perpendicularly under the X-ray tube 2 in such a way as to face the X-ray tube 2 in a state in which the loop belt 11 of the conveyer system 1 is interposed between the X-ray tube 2 and the one-dimensional X-ray detector 3.

The conveyer system 1 includes the loop belt 11, and a drive roller 12 and a plurality of driven rollers 13, over which the belt 11 is looped. A motor (not shown), which is adapted to rotate and drive in response to a drive signal supplied from a conveyer driver unit 14 by operating a switch provided on an operation unit 4, provides rotation to the drive roller 12. Rotation of the drive roller 12 causes the loop belt 11 to move under the guide of each of the rollers and to convey the object to be inspected W at a constant speed in a direction of an arrow in this figure.

A high-voltage generator 22 controlled by an X-ray controller 21 applies a high voltage to between an anode 2a and a cathode 2b of the X-ray tube 2, so that the X-ray tube 2 produces X-rays. A lead slit member 23 is provided between the X-ray tube 2 and the conveyer system 1. The lead slit member 23 has a slit 23a formed therein in such a way as to extend in a direction perpendicular to a conveying direction, in which the conveyer system 1 conveys the object to be inspected W. X-rays outputted from the X-ray tube 2 pass through the slit 23a thereby to produce X-ray fan beams each diverging in the direction of width of the conveyer system 1.

The one-dimensional X-ray detector 3 comprises a scintillator, and a MOS image sensor on which a plurality of devices are arranged like a line. Incident X-rays are converted by the scintillator into visual light, which is detected by each of the devices of the MOS image sensor in every very short constant time intervals. Each of the devices outputs a detection signal, whose level corresponds to an amount of incident X-ray radiation, every moment.

The detection signal outputted from each of the devices of the one-dimensional X-ray detector 3 is taken in by a data processor unit 5. The data processor unit 5 displays an X-ray perspective image, whose pixel gray level information is represented by the detection signal from each of the devices, on the screen of a monitor 51. Further, the data processor unit 5 determines, by performing a routine (to be described later) using data, which is outputted from each of the devices of the one-dimensional X-ray detector 3 every moment, whether or not a stockout of the object to be inspected occurs. Furthermore, according to a result of the determination, when it is decided that a stockout of the object occurs, data indicating such a decision is generated. Thus, as will be described later, an alarm buzzer 54 is sounded. Alternatively, an exclusion apparatus 55 is driven. Moreover, data representing such a decision is outputted to a data printer 52, and data representing such an image is outputted to a video printer 53.

Figure 2:
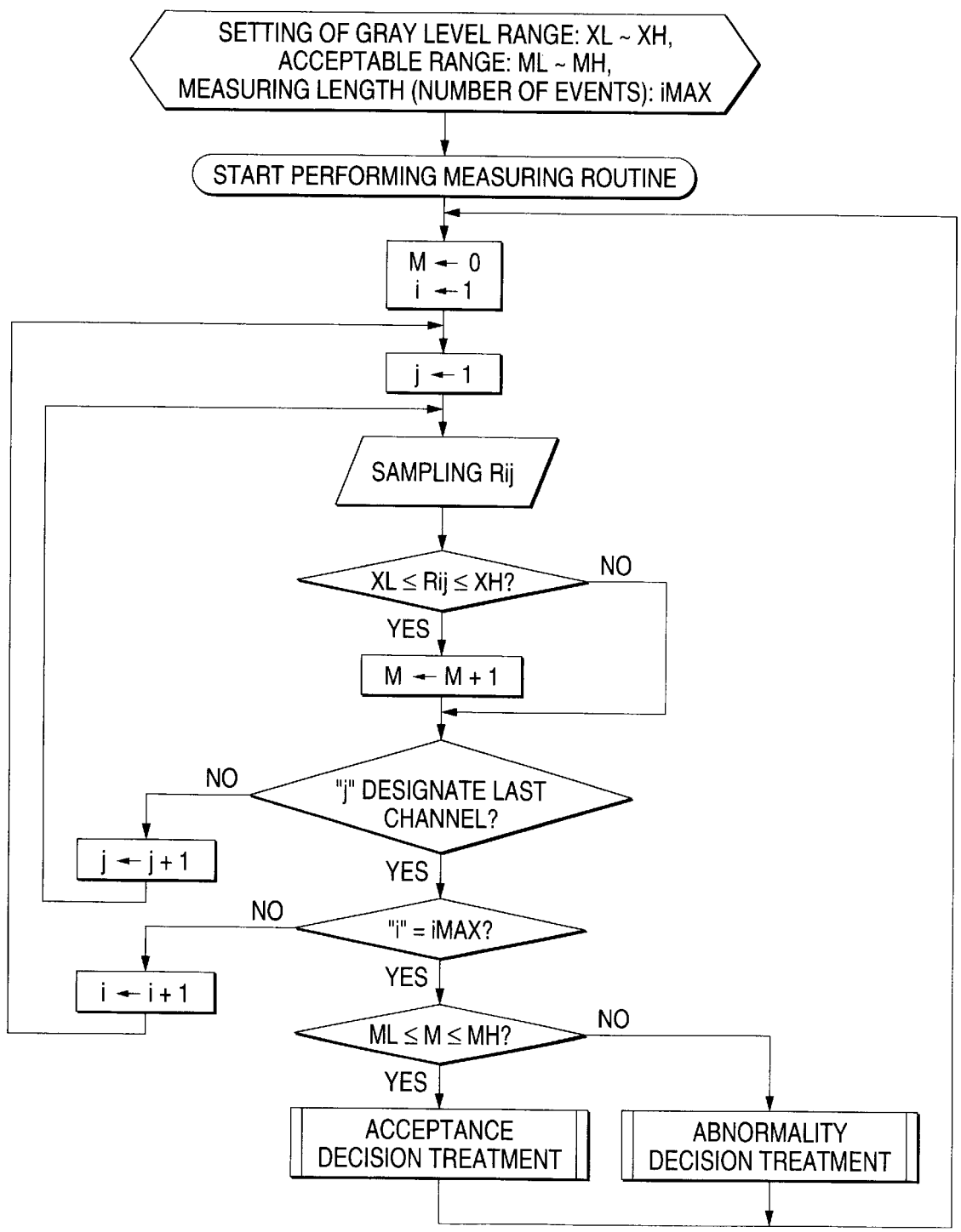
FIG. 2 is a flowchart illustrating a process for determining whether or not a stockout of object to be inspected occurs, which is performed by a data processor unit 5 according to the embodiment of the invention.
Figure 3A:
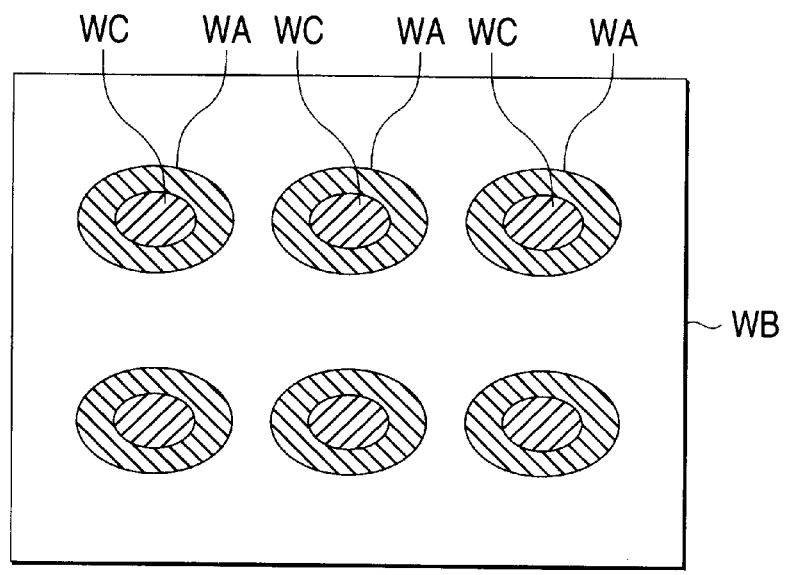
FIG. 3A is an explanatory view illustrating an example of an X-ray perspective image in the case of a normal state in which no lack of an object to be inspected W occurs.

FIG. 2 is a flowchart illustrating a process for determining whether or not a stockout of object to be inspected occurs, which is performed by the data processor unit 5. Hereinafter, an operation of determining in the embodiment of the invention whether or not a stockout occurs is described by referring to this FIG. 2. In this example, it is assumed that the data processor unit 5 determines whether or not a stockout occurs in six bean-jam buns WA accommodated in a packaging box WB, as shown in FIG. 3A illustrating an X-ray perspective image in a normal state. Incidentally, in FIG. 3A, reference character WC designates a bean-jam contained in the bean-jam bun WA. Further, in this flowchart, "i" designates an order of outputs of signals from the one-dimensional radiation detector 3 (that is, events), which are caused at very short constant time intervals, in other words, denotes time, and "j" designates No. of each of the devices (or channels) of the one-dimensional radiation detector 3. Therefore, each of pixels of an x-ray perspective image of the object to be inspected is represented by $R_{ij}$.

Figure 4:
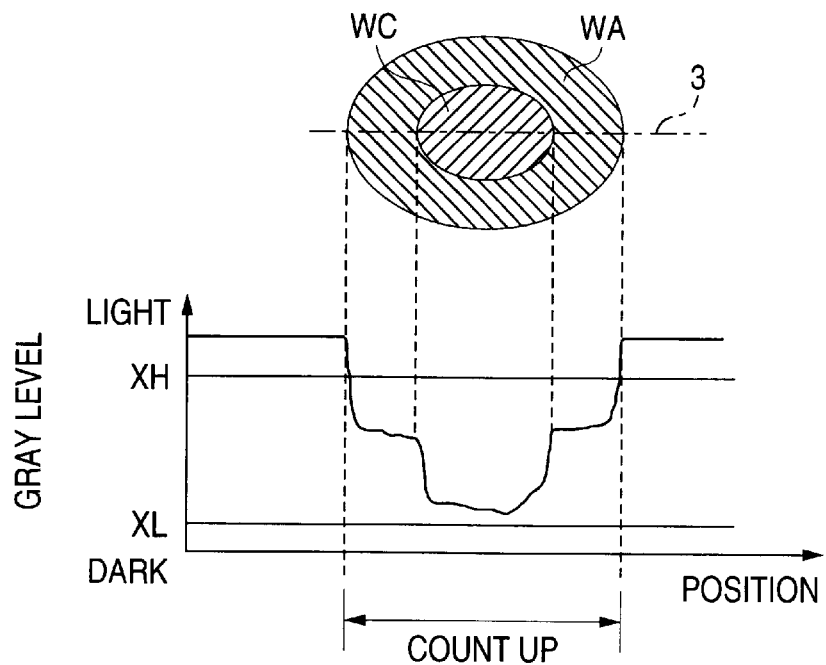
FIG. 4 is an explanatory view illustrating an example of setting a gray level range of gray level profile from XL to XH in the case of inspecting the object W shown in FIGS. 3A and 3B.

FIG. 4 illustrates the output (gray level) level of each of pixels while the state in which the one-dimensional X-ray detector 3 is positioned at the nearly central portion of the bean-jam bun WA. Meanwhile, before an automatic operation is performed, the lower limit XL and the upper limit XH of the gray level range of gray level profile of the pixels to be counted are set by operating the ten key provided in the operation unit 4. Further, this gray level range is set so that gray levels of all the pixels of the X-ray perspective image of the bean-jam bun are included therein, as is seen from FIG. 4, and that the gray levels of the pixels of a background image are not included therein. Moreover, the lower limit ML and the upper limit MH of the acceptance range for determining whether or not a stockout of the object occurs are set according to a result of counting the pixels having gray levels included in this gray level range.

Furthermore, the measuring length iMAX is set. This measuring length iMAX designates the number of detection signals outputted from the one-dimensional X-ray detector 3 correspondingly to the single object to be inspected W and taken in by the data processor unit 5. That is, the data processor unit 5 starts to take in outputs of the one-dimensional X-ray detector 3 in response to the generation of an external trigger signal outputted from a commodity detection sensor (not shown) when the leading end of the object to be inspected W having been conveyed on the conveyer system 1 reaches immediately in front of an X-ray irradiating position (i=1). When the number of the taken-in external trigger signals reaches the value of the measuring length iMAX, the data processor unit 5 finishes taking in the outputs of the one-dimensional X-ray detector 3.

Then, initiation of an automatic operation is commanded. Subsequently, the object to be inspected W is supplied onto the conveyer system 1. When the conveyer system 1 starts conveying the object W, initialization is performed in response to an output of the commodity detection sensor so that variables i, j, and M are set as follows i=1, j=1, and M=0. Here, M is a counter incremented by 1 when the gray level represented by the gray level information of each pixel is included in the set gray level range of gray level profile from XL to XH. Then, the data processor unit 5 takes in pixel information of each of pixels $R_{1j}$ in the case of the first event (that is, in the case that i=1). Then, the data processor unit 5 determines whether or not the gray level represented by the gray level information of each of pixels is included in the set gray level range of gray level profile from XL to XH, on the pixels respectively, which are taken in at i=1 and correspond to j of the devices of the one-dimensional X-ray detector 3, correspondingly to "j" whose value changes from 1 to No. of the last channel. In the case that the gray level information is included in the gray level range of gray level profile from XL to XH, M is incremented by 1.

Upon completion of determining correspondingly to each of all the channels whether or not the differential value is included in the gray level range, the data processor unit 5 next takes in pixel information of each of pixels $R_{2j}$ in the case of the second event (that is, in the case that i=2). The data processor unit 5 determines whether or not the gray level information of each of pixels respectively corresponding to all the channels is included in the set gray level range, similarly as the case that i=1. Then, at each occurrence of the gray level information included in the gray level range, M is incremented by 1. When the variable "i" reaches iMAX, it is decided whether or not the value M is included in the predetermined acceptance range of values ranging from ML to MH. Thus, it can correctly be known from this determination whether or not a stockout of the object to be inspected occurs.

Figure 3B:
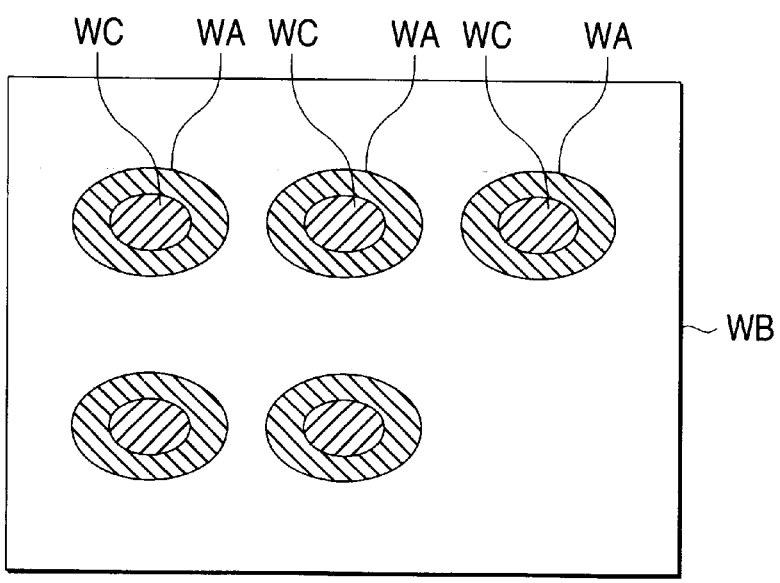
FIG. 3B is an explanatory view illustrating an example of an X-ray perspective image in the case of a state in which one lack of the object to be inspected W occurs.

That is, when the average number of pixels, whose gray levels are within the gray level range of gray level profile from XL to XH, of an X-ray perspective image of a single bean-jam bun WA is 100, the acceptance range of values from ML to MH is set at, for instance, about 540 to 660. In the case that six bean-jam buns are correctly contained the packaging box WB, as illustrated in FIG. 3A, the average of the numbers M is 600 and included within the acceptance range of values from ML to MH. Conversely, in the case that one bean-jam bun MA is missing in the packaging box WB, as illustrated in FIG. 3B, the average of the numbers M is 500 and thus not included in the acceptance range of values from ML to MH. Consequently, according to the invention, it can correctly be determined whether or not a stockout of the object occurs. Incidentally, in the case that the gray levels of the pixels of edge portions of the packaging box WB in the X-ray perspective image are included in the gray level range of gray level profile from XL to XH, the approximate number of such pixels is preliminarily estimated. Thus, it is sufficient that a number obtained by subtracting such an estimated number from the total number M is compared with the values between ML and MH of the acceptance range. Alternatively, it is sufficient that the acceptance range of the levels ML to MH is set by taking the number of pixels of edge portions of the packaging box WB into consideration.

When the number M is within the acceptance range of the values from ML to MH, an acceptance decision treatment is performed. Conversely, when the number M is not within the acceptance range of the values from ML to MH, an abnormality decision treatment, such sounding of an alarm buzzer or exclusion of a commodity, is performed. Thereafter, the inspection apparatus proceeds to determination on whether or not a stockout occurs in the next object to be inspected W.

The particularly noteworthy aspect of the aforementioned embodiment resides in that the acceptance decision is performed by totaling the number of pixels, whose gray levels are included in the preset gray level range, and deciding whether or not a result of the totalization is within the acceptance range, instead of performing the acceptance decision by image processing, which uses pixel data outputted from the one-dimensional X-ray detector 3, to thereby recognize a pattern of the bean-jam bun WA included in the object to be inspected W (or the packaging box WB). As compared with the case of software for the determination based on the pattern recognition, the software for the determination according to the invention, which employs such data processing, is extremely simple. Thus, the inspection apparatus of the invention has the advantageous effects that this apparatus can use relatively simple hardware for performing such software.

Incidentally, according to the invention, for instance, not only the number of the bean-jam buns WA contained in the packaging box WB, but also whether or not the bean-jam in each of the bean-jam buns WA is missing can be inspected by changing the setting of the gray level range of the gray level profile from XL to XH.

Figure 5:
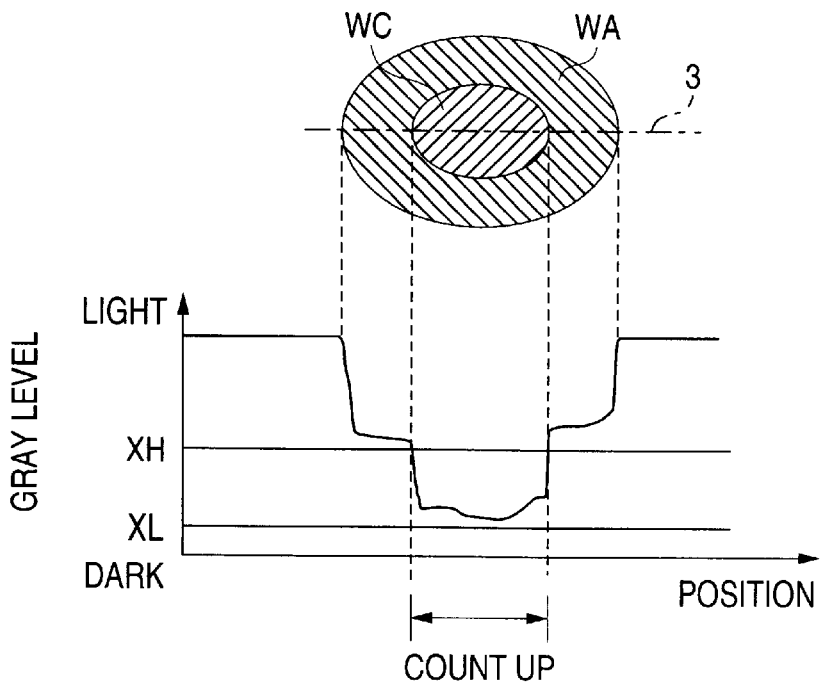
FIG. 5 is an explanatory view illustrating another example of setting a gray level range of gray level profile from XL to XH in the case of inspecting the object W according to the embodiment of the invention.
Figure 6:
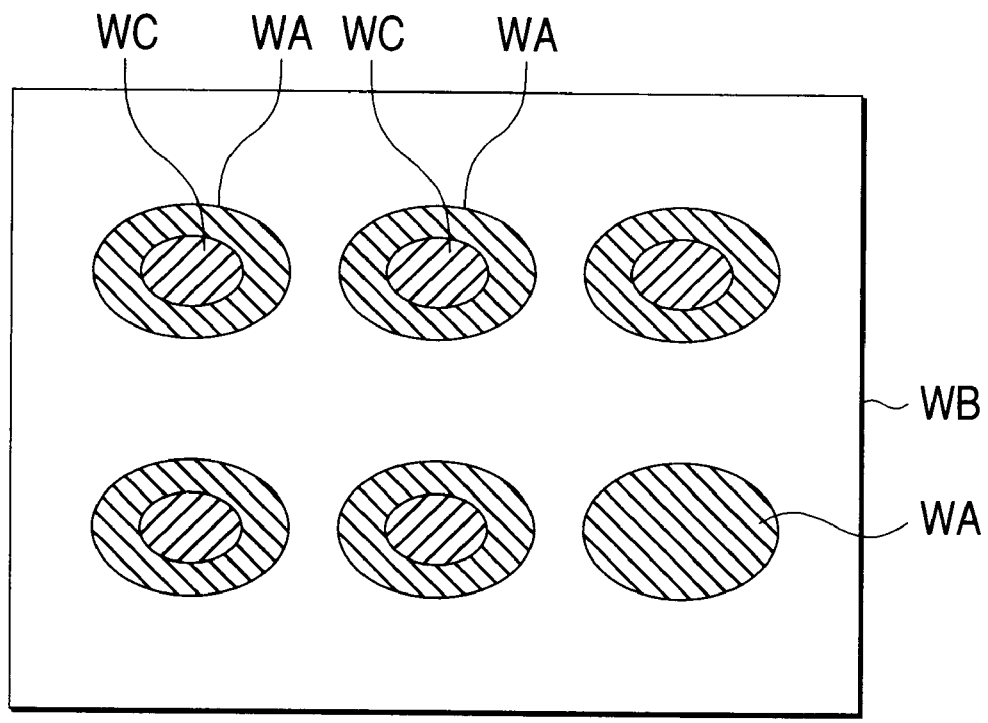
FIG. 6 is an explanatory view illustrating an X-ray perspective image of the object W to be used for inspecting a stockout thereof under conditions set as illustrated in FIG.

That is, as illustrated in FIG. 5, in an X-ray perspective image of the bean-jam bun WA, the gray levels of pixels of a perspective image of the inner bean-jam WC are thicker (or darker) than those of pixels of the circumferential coating of the bean-jam bun WA. Therefore, for example, in the case that the gray level range of gray level profile from XL to XH are set so that only the gray levels of the pixels of the bean-jam WC are included therein, that the average of the number of pixels of an X-ray perspective image of the bean-jam WC of the single bean-jam bun WA is 20, that six bean-jam buns are accommodated in a single packaging box WB of a commodity , similarly as the aforementioned commodity, and that the bean-jam WC is correctly included in all the bean-jam buns WA, as illustrated in FIG. 3A, the number M is about 120. Conversely, in the case that no bean-jam WC is contained in one of the bean-jam buns WA, the number M is about 100. Thus, whether or not a bean-jam WC is missing can correctly be determined by setting the acceptance range of values ML to MH at 105 to 135.

As described above, according to the invention, radiation is irradiated onto an object to be inspected. Thus, a perspective image of the object is obtained. Moreover, the number of pixels, whose gray levels are within a predetermined gray level range, is totalized. It can be determined by using a result of the totalization whether or not a stockout of the object occurs. Thus, the inspection apparatus of the invention can be used for inspection of object contained in a packaging container formed from a non-transmissive material, such as aluminum foil. Moreover, in the case of the inspection apparatus of the invention, data processing is easy to perform, as compared with the case that the inspection of the object is performed by recognizing a pattern of a radiation perspective image, similarly as a conventional foreign-object inspecting apparatus using radiation. Consequently, both the software and the hardware can be implemented at low cost. With low-cost configuration, the inspection apparatus of the invention can reliably determine whether or not a stockout of object, which are wrapped by a non-transmissive material, occurs.

What is claimed is:

1. A radiation inspection apparatus comprising:
   a radiation generator for generating radiation toward an object to be inspected;
   a radiation detector, disposed in such a way to face said radiation generator, for detecting the radiation transmitted through the object to be inspected and outputting a pixel gray level information for each pixel consisting an image of the object to be inspected; and a data processor unit for performing data processing by using the pixel gray level information outputted from said radiation detector, wherein said data processor unit totalizes the number of pixels, whose gray levels represented by the pixel gray level information, which is outputted from said radiation detector, are within a predetermined gray level range, and determines from a totalization of the number of pixels whether or not a stockout of the object to be inspected occurs.

2. The radiation inspection apparatus according to claim 1, further comprising:

a conveying unit for conveying the object to be inspected between said radiation generator and said radiation detector.

3. The radiation inspection apparatus according to claim 1, wherein said data processor unit determines that the stockout of the object to be inspected occurs when the totalization of the number of pixels is out of an acceptance range.

4. A radiation inspection method comprising:

generating radiation toward an object to be inspected;

detecting the radiation transmitted though the object to be inspected to obtain a pixel gray level information of each pixel consisting an image of the object to be inspected based on the detected radiation;

totalizing the number of pixels, whose gray levels represented by the pixel gray level information are within a predetermined gray level range; and determining from a totalization of the number of pixels whether or not a stockout of the object to be inspected occurs.

5. The radiation inspection method according to claim 4, wherein it is determined that the stockout of the object to be inspected occurs when the totalization of the number of pixels is out of an acceptance range.

* * * * *